United States Patent
Rong et al.

(10) Patent No.: US 10,772,580 B2
(45) Date of Patent: Sep. 15, 2020

(54) MULTIPLE EMISSION ENERGIES IN SINGLE PHOTON EMISSION COMPUTED TOMOGRAPHY

(71) Applicant: Siemens Medical Solutions USA, Inc., Malvern, PA (US)

(72) Inventors: Xing Rong, Schaumburg, IL (US); Jun Ma, Palatine, IL (US); Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 878 days.

(21) Appl. No.: 15/315,710

(22) PCT Filed: Jun. 12, 2015

(86) PCT No.: PCT/IB2015/054459
§ 371 (c)(1),
(2) Date: Dec. 1, 2016

(87) PCT Pub. No.: WO2015/189815
PCT Pub. Date: Dec. 17, 2015

(65) Prior Publication Data
US 2017/0086757 A1 Mar. 30, 2017

Related U.S. Application Data

(60) Provisional application No. 62/011,628, filed on Jun. 13, 2014.

(51) Int. Cl.
*A61B 6/03* (2006.01)
*G01T 1/164* (2006.01)
*A61B 6/00* (2006.01)

(52) U.S. Cl.
CPC .......... *A61B 6/037* (2013.01); *A61B 6/5258* (2013.01); *G01T 1/1647* (2013.01)

(58) Field of Classification Search
CPC ...... A61B 6/037; A61B 6/5258; G01T 1/1647
USPC ......................................... 600/436
See application file for complete search history.

(56) References Cited

U.S. PATENT DOCUMENTS

| | | | |
|---|---|---|---|
| 9,706,972 B1* | 7/2017 | Ahn | G06T 11/006 |
| 2006/0000983 A1* | 1/2006 | Charron | G01T 1/1641 |
| | | | 250/394 |
| 2007/0183642 A1 | 8/2007 | Ye et al. | |

(Continued)

FOREIGN PATENT DOCUMENTS

| | | |
|---|---|---|
| HU | P0800770 | 7/2010 |
| HU | P0900597 | 1/2011 |

OTHER PUBLICATIONS

Search Report for Corresponding Hungarian Patent Application No. P1700008, dated Mar. 23, 2017.

(Continued)

*Primary Examiner* — Sanjay Cattungal

(57) ABSTRACT

Single photon emission computed tomography (SPECT) is performed with multiple emission energies. For quantitative or qualitative SPECT, the image formation process for emissions at different energy ranges is modeled (44, 46, 48, 50) separately. Different scatter, different attenuation, and/or different collimator-detector response models corresponding to different energy ranges are used in the reconstruction.

18 Claims, 2 Drawing Sheets

(56) References Cited

U.S. PATENT DOCUMENTS

| | | | |
|---|---|---|---|
| 2008/0033291 A1* | 2/2008 | Rousso | A61B 6/486 600/436 |
| 2011/0164801 A1* | 7/2011 | Gagnon | G01R 33/481 382/131 |
| 2015/0185339 A1* | 7/2015 | Lage | G01T 1/2985 600/425 |
| 2018/0061031 A1* | 3/2018 | Rong | A61B 6/5205 |

OTHER PUBLICATIONS

Y. Du, et al. "Evaluation of simultaneous 201Tl/99mtc dual-isotope cardiac SPECT imaging with model-based crosstalk compensation using canine studies", Journal of Nuclear Cardiology, vol. 21, No. 2, Dec. 24, 2013, pp. 329-340.

PCT International Search Report and Written Opinion dated Oct. 9, 2015 (11 pages).

* cited by examiner

MULTIPLE EMISSION ENERGIES IN SINGLE PHOTON EMISSION COMPUTED TOMOGRAPHY

RELATED APPLICATIONS

The present patent document claims the benefit of the filing date under 35 U.S.C. § 119(e) of Provisional U.S. Patent Application Ser. No. 62/011,628, filed Jun. 13, 2014, which is hereby incorporated by reference.

BACKGROUND

The present embodiments relate to single photon emission computed tomography (SPECT). SPECT imaging uses a radioisotope or radiotracer to determine physiological function within a patient. For example, the uptake of the radiotracer by tissues in the body is measured. The emissions from the radiotracer are detected. The activity concentration (i.e., the concentration of the radiotracer from different locations) is reconstructed from the detected emissions.

For quantitative SPECT imaging, reliable (both accurate and precise) estimates of activity concentration and uptake values are desired. Given various modeling and unknowns in SPECT, general use of quantitative SPECT has been limited. For example, quantitative SPECT is only realized in industry for Tc-99m, which has a single emission energy. Quantitative imaging of radionuclides with multiple emissions (e.g., I-123, Lu-177 and In-111) or simultaneous imaging of multiple tracers (e.g. cardiac imaging for Tc-99m MIBI and I-123 MIBG) may have important applications in nuclear medicine, but the emissions at different energies may degrade the imaging.

BRIEF SUMMARY

By way of introduction, the preferred embodiments described below include methods, systems, and non-transitory computer readable media for single photon emission computed tomography (SPECT) with multiple emission energies, including both the discrete energy peaks such as Lu-177 and the continuous energy spectrum such as bremsstrahlung imaging for Y-90. For quantitative or qualitative SPECT, the emissions at different energies are modeled separately. Different energy ranges, windows with corresponding different scatter, different attenuation, and/or different collimator-detector response function models are used in the system matrix or forward projector.

In a first aspect, a method is provided for SPECT with multiple emission energies. A SPECT detector detects emissions from a patient where the emissions being at different energy ranges. The SPECT system reconstructs the patient or a part of the patient from projection data representing the emissions with modeling of the image formation process including models of the effects of scatter, attenuation, and collimator-detector response corresponding to each of the different energy ranges. An image of the patient or part of the patient is generated from the reconstruction.

In a second aspect, a non-transitory computer readable storage medium has stored therein data representing instructions executable by a programmed processor for SPECT with multiple emission energies. The storage medium includes instructions for modeling an effect of a first emission energy range in SPECT imaging of a patient, modeling an effect of a second emission energy range in the SPECT imaging of the patient, the second emission energy range different than the first emission energy range, and generating an image of the patient using the modeling of the effects of both the first and second emission energy ranges.

In a third aspect, a system is provided for SPECT with multiple emission energies. A SPECT system has a detector for detecting emissions. A processor is configured to form an image with a model treating two or more emission energy ranges of the emissions separately. A display is configured to display the image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

To accurately model the image formation process, different models are used for different "categories" of photons. The photons are categorized by their emission energy, their detection energy, and/or whether or not the photons are scattered in a patient. A specific model is chosen according to a pre-selected emission energy range, an acquisition energy window, and/or a specific physics process the photons undergo during the acquisition (e.g., whether photons are scattered in the patient).

Figure 2:
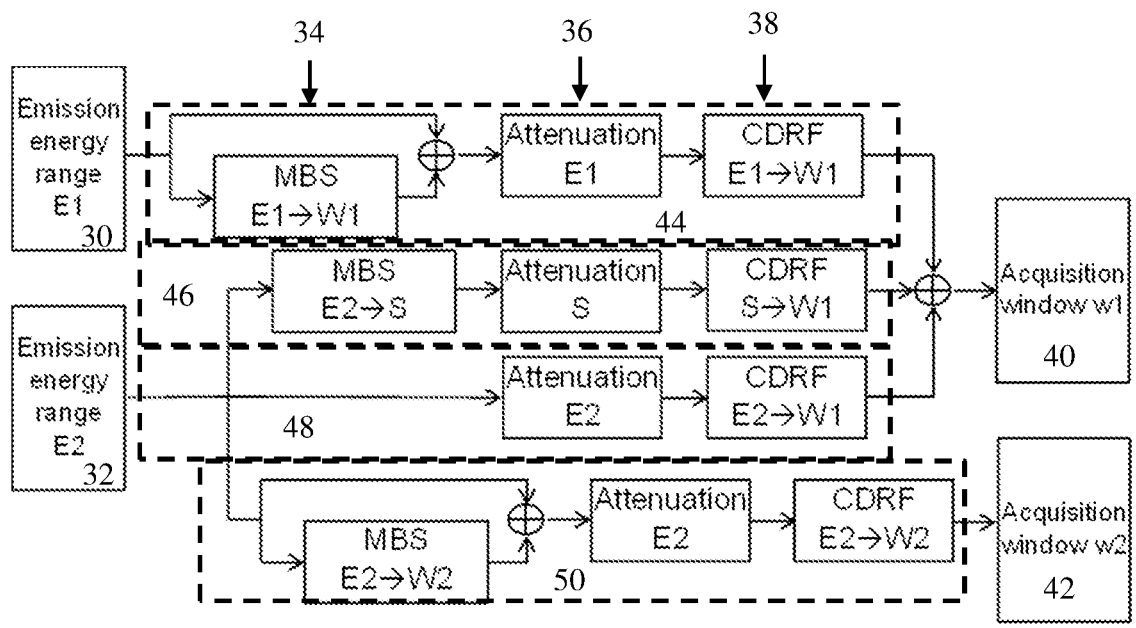
FIG. 2 is a representation of a model of image formation process in iterative SPECT reconstruction for multiple emission energies.

For radionuclides emitting multiple discrete energy peaks, one model may be applied for one emission peak or a combination of several peaks. For example, for Lu-177, in addition to two main peaks at 113 keV and 208 keV, there are two other minor peaks at 250 keV and 321 keV. Acquisition energy windows may not be provided around these two minor peaks, but the energies of the minor peaks may still contribute to the two acquisition energy windows around the two major peaks. In the example of FIG. 2, the emission energy range E2 may only include 208 keV, or alternatively, may include three peaks (208, 250 and 321 keV).

A SPECT detector detects emissions from a patient. The emissions have multiple discrete energy peaks (e.g., Lu-177) or a continuous energy spectrum (e.g., Y-90 bremsstrahlung photons). A SPECT system reconstructs images representing activity distribution in the patient from the acquired projection data using iterative algorithms. In each iteration, the image formation process including the effects of scatter, attenuation, and/or collimator-detector response is modeled separately for each category of photons. The categorization of photons is mainly determined by the emission energy, the acquisition energy window, and physics processes during the acquisition (e.g., whether or not photons are scattered in the patient).

Quantitative accuracy of iterative SPECT reconstruction is primarily determined by accuracy in the model of the image formation process. For radionuclides with emissions at multiple energies, the image degrading effects on an acquisition energy window from emissions with higher energies may be difficult to model accurately. In addition, energy dependence of various effects, such as attenuation, scatter and collimator-detector response, imposes further challenges on accurate modeling.

A physics-based modeling method is applicable to quantitative imaging of radionuclides with multiple emissions or simultaneous imaging of multiple tracers. Energy dependence of various image-degrading effects (e.g., attenuation, scatter and collimator-detector response) is accounted for by separating the modeling of these effects based on photon energies. Both image quality and quantitative accuracy for SPECT imaging of radionuclides with multiple emissions (e.g., I-123, Lu-177 and In-111) and simultaneous imaging of multiple tracers may be improved.

In one embodiment, the scatter is more accurately modeled at the different energies using physics-based methods. Monte Carlo simulation may facilitate more accurate modeling for both scatter and collimator-detector response at the different energies.

Figure 1:
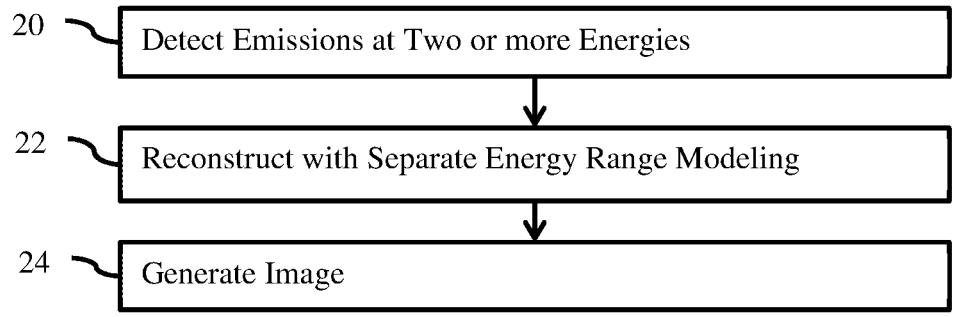
FIG. 1 is a flow chart diagram of one embodiment of a method for SPECT imaging with multiple emission energies.

FIG. 1 shows one embodiment of a method for SPECT imaging with multiple emission energies. Separate energy ranges and corresponding models for scatter, attenuation, and/or collimator-detector response function are used to more accurately quantify the activity distribution.

The method is applied for a given scan of a given patient. By using the different models for different energies, multiple tracers and/or radioisotopes that generate emissions at multiple energies may be used at a same time in SPECT imaging of a patient. By using multiple acquisition energy windows for the same radionuclide, the noise may be reduced. As a result, the image quality and precision of quantifying the activity distribution may be improved. Alternatively or additionally, the imaging time and/or patient dose may be reduced and patient throughput may be increased. Simultaneous imaging of multiple radiotracers may eliminate mis-registration, reduce motion artifacts, and/or increase throughput.

Additional, different, or fewer acts may be performed. For example, act 20 is not provided where the detected emissions are stored or transferred from memory. As another example, act 24 is not provided where the reconstructed object is used for purposes other than imaging, such as to calculate a quantity. In other examples, acts related to positioning the patient, configuring the SPECT scanner, and/or SPECT imaging are provided. The acts are performed in the order shown or a different order.

In act 20, emissions from a patient are detected. The activity concentration in a patient having received a radiotracer or radiotracers is determined as part of reconstruction by a SPECT system. After ingesting or injecting the radiotracer or tracers into the patient, the patient is positioned relative to a SPECT detector, and/or the SPECT detector is positioned relative to the patient. Emissions from the radiotracer or tracers within the patient are detected over time. A collimator in front of the detector limits the direction of photons detected by the SPECT detector, so each detected emission is associated with an energy and line or cone of possible locations from which the emission occurred. The lateral position of the line or cone relative to the detector may likewise be determined. The SPECT detector may be rotated or moved relative to the patient, allowing detection of emissions from different angles and/or locations in the patient.

The SPECT detector includes photomultiplier tubes or other photon detectors layered with a scintillation crystal. The photomultiplier tubes are arranged along a rectangular or other grid to provide a two-dimensional planar array for detecting gamma radiation. Other types of detectors may be used, such as any gamma detector.

The emissions are at different energies. Energies at two or more levels are detected. The energies are for chosen ranges whether ranges from a continuous energy spectrum, from different major peaks, and/or from different minor peaks. For example, for I-123, there is a single main emission energy peak at 159 keV and a lot of minor emission high energy peaks. Rather than use a single photon peak acquisition energy window around 159 keV, two models are used in reconstruction—one for emission energy peak 159 keV and another for all high energy emission peaks. These two models have exactly the same acquisition energy window but different emission energies. In one embodiment, the emissions are generated by two or more radiotracers. Each radiotracer causes emissions at a different energy, such as using Tc-99m MIBI and I-123 MIBG for cardiac imaging. Any combination of two or more radiotracers may be used for a given scan of a patient (i.e., at a same time). In another embodiment, a radionuclide with different emission energies is used. For example, I-123, Lu-177 or In-111 is used. Lu-177 emits with energy peaks at 113 kv and 208 kv. The other peaks may not be included or may be included within the energy range set around one of the peaks being used.

The scatter from the higher energy may interfere or contribute to the emissions detected at the lower energy. Scatter in the patient and/or collimator-detector may cause a loss of energy, resulting in the scatter from the higher energy having a detectable energy near the lower energy. To determine the locations within the patient at which the emissions occurred, the detected emissions are reconstructed into an object space. The reconstruction may be less accurate due to emissions at different energy ranges.

In act 22, reconstruction is performed using the acquired projection data. The projection data represents the detected emissions. A processor of a SPECT system reconstructs the image that represents the activity distribution in patient. The quantity or amount of uptake for each location (e.g., voxel) is estimated as part of the reconstruction. The SPECT imaging system estimates the activity concentration of an injected radiopharmaceutical or tracers for the different locations. In quantitative SPECT, the goal is to estimate the activity concentration in kBq/ml of the tracer (i.e., isotope) that was injected into and distributed within the patient.

The reconstruction is iterative. Reconstruction includes a projection operator (i.e., forward projector) that incorporates the effects of the gamma camera on the photons (i.e., collimation and detection process). Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, non-negative least squares (NNLS), or another approach.

In the reconstruction, the forward projector contains a model of the imaging formation process. The image formation model includes the interaction of photons with patients (e.g., attenuation and scatter), the collimation-detection process (e.g., collimator detector response including collimator geometric response, septal penetration and scatter, partial deposition in crystal and detector intrinsic resolution), and related radionuclide properties (e.g., emission abundances). One mathematical representation of the forward projector is provided by:

$$\begin{bmatrix} Y_1 \\ Y_2 \\ Y_3 \\ \vdots \end{bmatrix} = \begin{bmatrix} H_{11} + H_{12} + H_{13} + \ldots \\ H_{21} + H_{22} + H_{23} + \ldots \\ H_{31} + H_{32} + H_{33} + \ldots \\ \vdots \end{bmatrix} I$$

where $Y_i$ is the projection data for ith acquisition window, $H_{ij}$ is the system matrix for ith acquisition window and jth component of model of image formation process, and I is the reconstructed image or object (i.e., part of the patient). Other representations may be used.

The system matrix is the mathematical representation of the projection from the object space to the projection space (e.g., forward projector). In some SPECT systems such as SPECT for small animal imaging, the system matrix is actually stored and used directly in each iteration to calculate the projection data model from current estimate of the activity distribution. In most clinical SPECT systems, due to the very large dimension of the system matrix, the system matrix is not stored. Instead, a series of mathematical operators, collectively called the forward projector, are performed in each iteration, which mathematically provides multiplication by the system matrix.

For use with emissions at two or more energies, since the various image degrading effects (e.g., scatter, attenuation, and/or collimator-detector response function) are different for different energy ranges, in the forward projector the image formation process for photons at different energy ranges is modeled separately. In one embodiment, scatter, attenuation, and collimator-response functions are modeled separately for each of the different emission energies, emission energy ranges, and/or acquisition energy windows. One model that handles the scatter, attenuation, and/or collimator-response function differently for different energy provides separate models.

Any type of scatter model may be used. Model-base scatter estimation is provided by modeling the physics of scatter in the patient. A Monte-Carlo simulation or other simulation may be used. Other physics or types of modeling of scatter may be used. The scatter may be modeled differently for different energies. Photons with different energies may scatter differently.

Any type of attenuation model may be used. For example, attenuation coefficients as a function of three-dimensional location in the patient are estimated from anatomical information provided by computed tomography (CT). The attenuation as emitted photons travel through tissue of the patient is modeled using the measured attenuation coefficients. Different energies attenuate differently, which may be modeled as different attenuation coefficients for different energies or a different scaling factor for the different energies. Other models of attenuation may be used.

Any type of collimator-detector response function model may be used. In one embodiment, point response functions are measured for the specific collimator and detector or for a class (i.e., type of collimator-detector pair). A Monte-Carlo or other simulation may be used. The point response function varies as a function of energy level. Other collimator-detector response functions may be used.

FIG. 2 shows one example embodiment of modeling separately for different energy ranges. In the example of FIG. 2, four channels 44, 46, 48, 50 for modeling are provided, but additional, different, or fewer channels may be provided. Two of the channels 46, 48 model contribution of a higher energy to detected emissions at the lower energy. Two other channels 44, 50 model for the different acquisition windows 40, 42 for the different energy ranges E1, E2, respectively. Any channel configuration may be used to provide the separate modeling by energy. By starting with different models for the different energy ranges E1, E2, separate modeling is provided. The separate modeling is provided regardless of using separate acquisition windows 40, 42 and regardless of which of the specific scatter, attenuation, and collimator-detection response functions are different as a function of energy. In the example of FIG. 2, the reconstruction uses different acquisition windows 40, 42 for the different energies. If both acquisition windows 40, 42 are for the same radionuclide, the windows 40, 42 are used together to reconstruct a single image for the radionuclide. For simultaneous imaging of multiple tracers, if each window 40, 42 corresponds to a different tracer, the windows 40, 42 are also used together to reconstruct two images, each of which represents each tracer. Separate modeling may be provided with or without modeling contribution from the higher energy to the lower energy (e.g., with or without channels 46 and/or 48).

FIG. 2 shows emissions of energy in two different ranges 30, 32. Each range corresponds to expected peak emissions, such as 113 kv and 208 kv for Lu-177, with or without including other peaks, and/or corresponds to any chosen ranges that are different (e.g., selecting two ranges in a continuous energy spectrum). The ranges are exclusive (i.e., do not overlap) or overlap. For imaging of a single tracer, the energy ranges of emissions from a single tracer are exclusive. When imaging multiple tracers, different tracers belong to different categories regardless whether the emission energy ranges overlap or not. For radionuclides with discrete energy peaks, the so-called emission energy range is either a single energy peak or a set of energy peaks. For example, for Lu-177, E2 may be a single energy peak 208 keV, or a set of three peaks 208, 250 and 321 keV. Range generalizes to also include the situation of continuous energy spectrum such as Y-90 bremsstrahlung photons.

Where the emissions at the different energies are used to measure activity concentration separately, the separate acquisition windows 40, 42 are provided for the different energy ranges 30, 32. In other embodiments, such as for imaging a single tracer, projection data from multiple windows are used together to reconstruct a single image. The effect of emissions in the lower energy range 30 is modeled for SPECT imaging of the patient. The physics-based modeling includes the scatter model 34, attenuation model 36, and collimator-detector response function model 38 in the channel 44. Similarly, the effect of emissions in the higher energy range 32 is modeled for SPECT imaging of the patient. The physics-based modeling includes the scatter model 34, attenuation model 36, and collimator-detector response function model 38 in the channel 50. The modeling of scatter, attenuation, and collimator-detector response function are treated separately. The effect of the lower emission energy range 30 is modeled separately from the effect of the higher emission energy range 32.

Two branches are shown in channel 44. The direct branch corresponds to detected primary photons (i.e., photons that are not scattered in the patient) from emission energy range E1. In the other branch (scatter modeling 34), the scatter model from the energy range E1 to the acquisition window W1 models detected emissions caused by scattering of the lower energy in the patient. The detected emissions from both sources are summed. The attenuation modeling 36 is applied, followed by application of the collimator-detector response function 38. The collimator-detector response function 38 models the effects of collimator geometric response, septal penetration and scatter, partial deposition in crystal, detector intrinsic resolution, and/or backscatter from structures behind crystal. For channel 50, the same model arrangement is used, but for the energy range E2 and the respective acquisition window W2.

Channel 46 models the image formation process for photons that are emitted from energy range E2, scattered in the patient, and then detected in lower energy acquisition window W1. Since Compton scatter reduces the energy, scattering from higher energy emissions may contribute to detections at the lower acquisition energy window. Some higher energy emissions scatter in the patient, so the scatter model 34 is provided for separately modeling scatter 34 from E2 to energy range S. Energy range S refers to the energy range where scattered photons from emission energy range E2 may contribute to detected photons in the acquisition window W1. These scattered photons attenuate traveling in the patient, so the attenuation for the energy range S is modeled 36. The scattered photons impinge upon the collimator and detector, so the collimator-detector response function for the effects from S to W1 is also modeled 38.

Channel 48 models the image formation process for photons that are emitted from energy range E2, unscattered in the patient, and then detected in lower energy acquisition window W1. The reduction in energy results from collimator scatter, partial deposition in crystal, and backscatter from structures behind the crystal. Since the photons are not scattered in the patient, a scatter model 34 is not provided in channel 48. The attenuation for the higher energy range E2 is modeled 36, and the collimator-detector response function modeling the effects from E2 to W1 is modeled 38 in this channel 48.

In the example of FIG. 2, the model of image formation process incorporates the effects of high energy range E2 on low energy acquisition window W1. The reduction in energy results from both the scattering in the patient and the interactions in the camera. The scattering in the patient is modeled in channel 46, and the interactions in the camera are modeled both in channel 46 and channel 48. The difference between channel 46 and 48 is whether or not the photons are scattered in the patient. The acquisition window 40 represents detected photons in W1 from (1) emissions from the low energy range E1 including both primary and scattered photons, (2) in-patient scattering with following collimator-detector interactions for emissions from high energy range E2, and (3) emissions from higher energy range E2 direct to collimator-detector interactions (unscattered in patient). In alternative embodiments, either or both of channels 46 and 48 are not provided.

Referring to FIG. 1, an image of the patient or part of the patient is generated from the reconstruction in act 24. The reconstruction provides voxel values representing activity concentration. The distribution in two or three dimensions of the activity concentration in the object is reconstructed. Alternatively, the reconstruction is direct to the image space, such as reconstructing the activity concentration for a plane or projection to a plane.

An image is generated from the reconstructed object (e.g., whole patient or part of the patient). In one embodiment, data for one or more (e.g., multi-planar reconstruction) planes is extracted (e.g., selected and/or interpolated) from a volume or voxels and used to generate a two-dimensional image or images. In another embodiment, a three-dimensional rendering is performed. Projection or surface rendering is used to create a representation of the volume or part of the patient from a given viewing direction on the two-dimensional screen.

The image is a quantitative SPECT image. Any quantitative SPECT imaging may be provided, such as providing an image where the user may determine a value for activity concentration for any selected location represented in the image. Alternatively, the image is a qualitative SPECT image that indicates relative activity concentration distribution in the patient. Any SPECT image may be displayed alone, adjacent to a computed tomography (CT) image, or overlaid on a CT image (e.g., color for SPECT and grayscale for computed tomography). Multi-modality images with magnetic resonance, ultrasound, x-ray, or other modalities may be used.

Where two or more tracers are used, the different tracers may be associated with different physiological functions. Where the tracers have different energy of emission, the dual-energy image may show the spatial distribution and/or activity concentration for the different functions. Similarly, uptake distribution and therapy dose distribution from a same multi-energy emission tracer may be presented.

Figure 3:
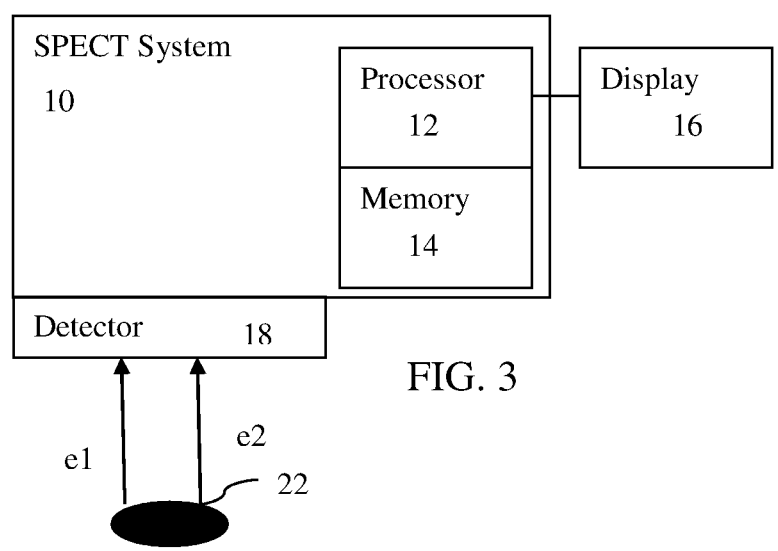
FIG. 3 is a block diagram of a system, according to one embodiment, for SPECT imaging with multiple emission energies.

FIG. 3 shows a system for SPECT imaging with multiple emission energies. The system implements the method of FIG. 1, the model of FIG. 2, or other method and/or model.

The system includes an SPECT system 10, a processor 12, a memory 14, and a display 16. The processor 12, memory 14, and/or display 16 are part of the SPECT system 10 or are separate (e.g., a computer or workstation). Additional, different, or fewer components may be provided. For example, the system is a computer without the SPECT system 10. As another example, user input, patient bed, or other SPECT related devices are provided. Other parts of the system may include power supplies, communications systems, and user interface systems.

The SPECT system 10 includes a detector 18. Other components may be provided, such as collimator. Any now known or later developed SPECT system 10 may be used.

The detector 18 is a gamma camera connected with a gantry. The gamma camera is a planar photon detector, such as having crystals or scintillators with photomultiplier tubes or other optical detector. The gantry rotates the gamma camera about the patient. During scanning of a patient, emission events are detected with the camera at different positions or angles relative to the patient.

The SPECT system 10, using the detector 18, detects emissions from the patient 22 for measuring uptake or physiological function. The detector 18 detects emissions at different energies e1, e2 from the patient 22, but may detect for only one energy range. For imaging uptake in a patient, the detector 18 detects emissions from the patient. The emissions occur from any location in a finite source (i.e., the patient). The radiotracer in the patient migrates to, connects with, or otherwise concentrates at specific types of tissue or locations associated with specific biochemical reactions. As a result, a greater number of emissions occur from locations of that type of tissue or reaction.

The SPECT system 10, using the processor 12 or another processor, is configured to reconstruct the imaged volume from the detected data. Any reconstruction may be used to estimate the activity concentration or distribution of the tracer or tracers in the patient. The processor 12 performs the reconstruction, or the SPECT system 10 has another processor that performs the reconstruction. The SPECT system 10 accesses the detected emission events from the memory 14, from the detector 18, or buffers to reconstruct.

The forward projector used by the processor 12 includes a model treating two or more emission energy ranges separately. The model accounts for scatter in the patient, attenuation in the patient, and collimator-detector response as a function of energy. Different models are provided for different energies and/or a given model accounts for differences due to different levels of energy. In one embodiment, the more counts provided by the different acquisition windows are used together to increase the count, reducing noise in the resulting reconstructed image. In another embodiment, the model accounts for the effects of emissions from the higher energy ranges on a lower energy acquisition window due to scatter in the patient and interactions in the camera.

The processor 12 generates one or more images based on the reconstruction. Any given image represents the emissions from the two or more energies. The different acquisition windows may be used to reduce noise by increasing the detected counts from the radiotracer. Where multiple radiotracers are used, images for the different radiotracers may be generated differently, such as in adjacent representations (e.g., screen with rendering from radiotracer A next to rendering from radio tracer B) or by color coding. In yet other embodiments, the image represents emissions from one energy range, but the represented uptake or activity concentration accounts for undesired detection in that energy range caused by scattering from emissions at the higher energy range.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions, such as one processor (e.g., application specific integrated circuit or field programmable gate array) for reconstructing and another for generating an image. In one embodiment, the processor 12 is a control processor or other processor of SPECT system 10. In other embodiments, the processor 12 is part of a separate workstation or computer.

The processor 12 operates pursuant to stored instructions to perform various acts described herein, such as reconstructing of act 22 and generating an image of act 24. The processor 12 is configured by software, firmware, and/or hardware to reconstruct with models of the image formation process separately for different energy ranges and/or acquisition windows.

The detected emission events, energy level, location, or other SPECT detection information are stored in the memory 14. The memory 14 may store data at different stages of processing, such as counts, raw data representing detected events without further processing, filtered or thresholded data prior to reconstruction, reconstructed data, filtered reconstruction data, system matrix, projection data, thresholds, an image to be displayed, an already displayed image, a forward projection, a backward projection, a measure of completeness of reconstruction, or other data. The data is stored in any format. The memory 14 is a buffer, cache, RAM, removable media, hard drive, magnetic, optical, database, or other now known or later developed memory. The memory 14 is a single device or group of two or more devices. The memory 14 is part of SPECT system 10 or a remote workstation or database, such as a PACS memory.

The memory 14 is additionally or alternatively a non-transitory computer readable storage medium with processing instructions. The memory 14 stores data representing instructions executable by the programmed processor 12. The instructions for implementing the processes, methods, and/or techniques discussed herein are provided on non-transitory computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 16 is a CRT, LCD, plasma screen, projector, printer, or other output device for showing an image. The display 16 displays an image of the reconstructed functional volume, such as showing activity concentration as a function of location. The uptake function of the tissues of the patient is represented in the image. The uptake for different tracers having different energy levels may be represented. Multi-planar reconstruction, 3D rendering, or cross-section imaging may be used to generate the image from the voxels of the reconstructed volume. Alternatively or additionally, any quantities derived by the processor 12 may be displayed, such as uptake values and/or change in uptake value. Other quantities may be determined, such as average uptake value or activity concentration for a region, maximum uptake value, peak uptake value in a predetermined unit volume, variance in activity concentration, or total uptake.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for single photon emission computed tomography (SPECT) with multiple emission energies, the method comprising:
   detecting with a SPECT detector, emissions from a patient, the emissions being at different energy ranges;
   reconstructing by a SPECT system, the patient or a part of the patient from projection data representing the emissions with modeling of an image formation process including separate models of effects of scatter, attenuation, and collimator-detector response corresponding to each of the different energy ranges; and generating an image of the patient or part of the patient from the reconstruction.

2. The method of claim 1 wherein the detecting comprises detecting the emissions from a radionuclide with the different emission energies, the radionuclide being in the patient.

3. The method of claim 1 wherein the detecting comprises detecting the emissions from multiple tracers in the patient.

4. The method of claim 1 wherein the reconstructing comprises reconstructing with the models of the scatter being a model-based, the models of the attenuation being based on computed tomography measures of the part, and the models of the collimator-detector response function including a point response function.

5. The method of claim 1 wherein the reconstructing comprises reconstructing with the models of the scatter, attenuation, and collimator-detector response function each corresponding to one of the different energy ranges and a corresponding acquisition energy window.

6. The method of claim 1 wherein the reconstructing comprises reconstructing with the modeling for a first energy range of the different energy ranges including contribution in an energy window for the first energy range from the emissions at a second energy range of the different energies due to scatter in the patient.

7. The method of claim 1 wherein the reconstructing comprises reconstructing with the modeling for a first energy range of the different energy ranges including contribution in an energy window for the first energy range from the emissions at a second energy range of the different energy ranges due to interactions in a collimator, detector, or collimator and detector.

8. The method of claim 7 wherein the reconstructing comprises reconstructing with the modeling for the first energy range including an additional contribution in the energy window for the first energy range from the emissions at the second energy range due to scatter in the patient.

9. The method of claim 1 wherein the reconstructing comprises reconstructing with different acquisition windows for the different energy ranges, the modeling of the image formation process being separate for the different acquisition windows.

10. The method of claim 1 wherein the generating the image comprises generating an quantitative SPECT image.

11. The method of claim 1 wherein the generating the image comprises generating the image from counts based on the different energy ranges.

12. In a non-transitory computer readable storage medium having stored therein data representing instructions executable by a programmed processor for single photon emission computed tomography (SPECT) with multiple emission energies, the storage medium comprising instructions for:
separately modeling effects of scatter, attenuation and collimator-detector response corresponding to a first emission energy range in SPECT imaging of a patient;
separately modeling effects of scatter, attenuation and collimator-detector response corresponding to a second emission energy range in the SPECT imaging of the patient, the second emission energy range different than the first emission energy range; and
generating an image of the patient using the modeling of the effects of scatter, attenuation and collimator-detector response of both the first and second emission energy ranges.

13. The non-transitory computer readable storage medium of claim 12 wherein the separately modeling the effects of scatter, attenuation and collimator-detector response of the first and second emission energy ranges comprises physics-based modeling.

14. The non-transitory computer readable storage medium of claim 12 further comprising modeling a scatter-based contribution of emissions in the second emission energy range to detections in the first emission energy range.

15. The non-transitory computer readable storage medium of claim 14 wherein the modeling the scatter-based contribution comprises modeling (1) a first contribution of scatter in the patient and collimator-detector scatter from the scatter in the patient and (2) a second contribution of collimator-detector scatter from the emissions in the second emission energy range.

16. The non-transitory computer readable storage medium of claim 12 wherein the generating the image comprises generating a quantitative SPECT image of physiological function with two or more tracers.

17. A system for single photon emission computed tomography (SPECT) with multiple emission energies, the system comprising:
a SPECT system with a detector for detecting emissions;
a processor configured to form an image with separate models of effects of scatter, attenuation and collimator-detector response corresponding to each of two or more different emission energy ranges of the emissions; and
a display configured to display the image.

18. The system of claim 17 wherein the processor is configured to form the image with one of the separate models of the effects for a first of the emission energy ranges accounting for patient and collimator-detector scatter from emissions in a second of the emission energy ranges contributing to detection in the first emission energy range.

* * * * *